United States Patent
Ouchene et al.

(10) Patent No.: US 7,270,642 B2
(45) Date of Patent: Sep. 18, 2007

(54) DEVICE FOR APPLYING CONTROLLED AND ADJUSTABLE COMPRESSION TO A LIMB

(75) Inventors: Amina Ouchene, Maisons-Alfort (FR); Jean-Louis Counord, Rueil-Malmaison (FR)

(73) Assignee: Laboratoires Innothera, Arcueil (FR)

( * ) Notice: Subject to any disclaimer, the term of this patent is extended or adjusted under 35 U.S.C. 154(b) by 210 days.

(21) Appl. No.: 10/518,094

(22) PCT Filed: Jun. 18, 2003

(86) PCT No.: PCT/FR03/01850

§ 371 (c)(1),
(2), (4) Date: Aug. 16, 2005

(87) PCT Pub. No.: WO04/000183

PCT Pub. Date: Dec. 31, 2003

(65) Prior Publication Data

US 2006/0036203 A1 Feb. 16, 2006

(30) Foreign Application Priority Data

Jun. 19, 2002 (FR) .................................. 02 07520

(51) Int. Cl.
*A61H 9/00* (2006.01)
(52) U.S. Cl. ...................... 601/151; 601/148; 601/150; 128/DIG. 20
(58) Field of Classification Search ................ 601/148, 601/149, 150, 151, 152; 602/13, 23; 128/DIG. 20
See application file for complete search history.

(56) References Cited

U.S. PATENT DOCUMENTS

| 2,747,570 | A |   | 5/1956 | Jobst |
| 3,826,249 | A |   | 7/1974 | Lee |
| 3,908,642 | A |   | 9/1975 | Vinmont |
| 4,206,751 | A |   | 6/1980 | Schneider |
| 5,403,265 | A | * | 4/1995 | Berguer et al. ............. 601/151 |
| 6,945,944 | B2 | * | 9/2005 | Kuiper et al. ................. 602/13 |

FOREIGN PATENT DOCUMENTS

| FR | 2 616 064 | 12/1988 |
| WO | WO 02/19955 | 3/2002 |

* cited by examiner

Primary Examiner—Quang D. Thanh
(74) Attorney, Agent, or Firm—Jacobson Holman PLLC

(57) ABSTRACT

A tubular sleeve (40) comprises an anterior portion (16) of inextensible material that comes to bear against the tibial ridge, and a posterior portion (18) of extensible material covering the region to be compressed. These two portions are connected together along two connection generator lines (20). Inflatable balloons (22) are disposed on the inside face of the anterior portion, being interposed between the inextensible material and the tibial crest. Means (24, 26, 28) are provided for inflating each of the balloons differently to a respective given pressure so as to apply deformation to the anterior portion of the sleeve that is suitable for inducing a traction force that is exerted on the extensible posterior portion; this force is distributed regularly along the generator lines and acts perpendicularly thereto, and consequently leads to compression action on the compressible region of the limb.

8 Claims, 1 Drawing Sheet

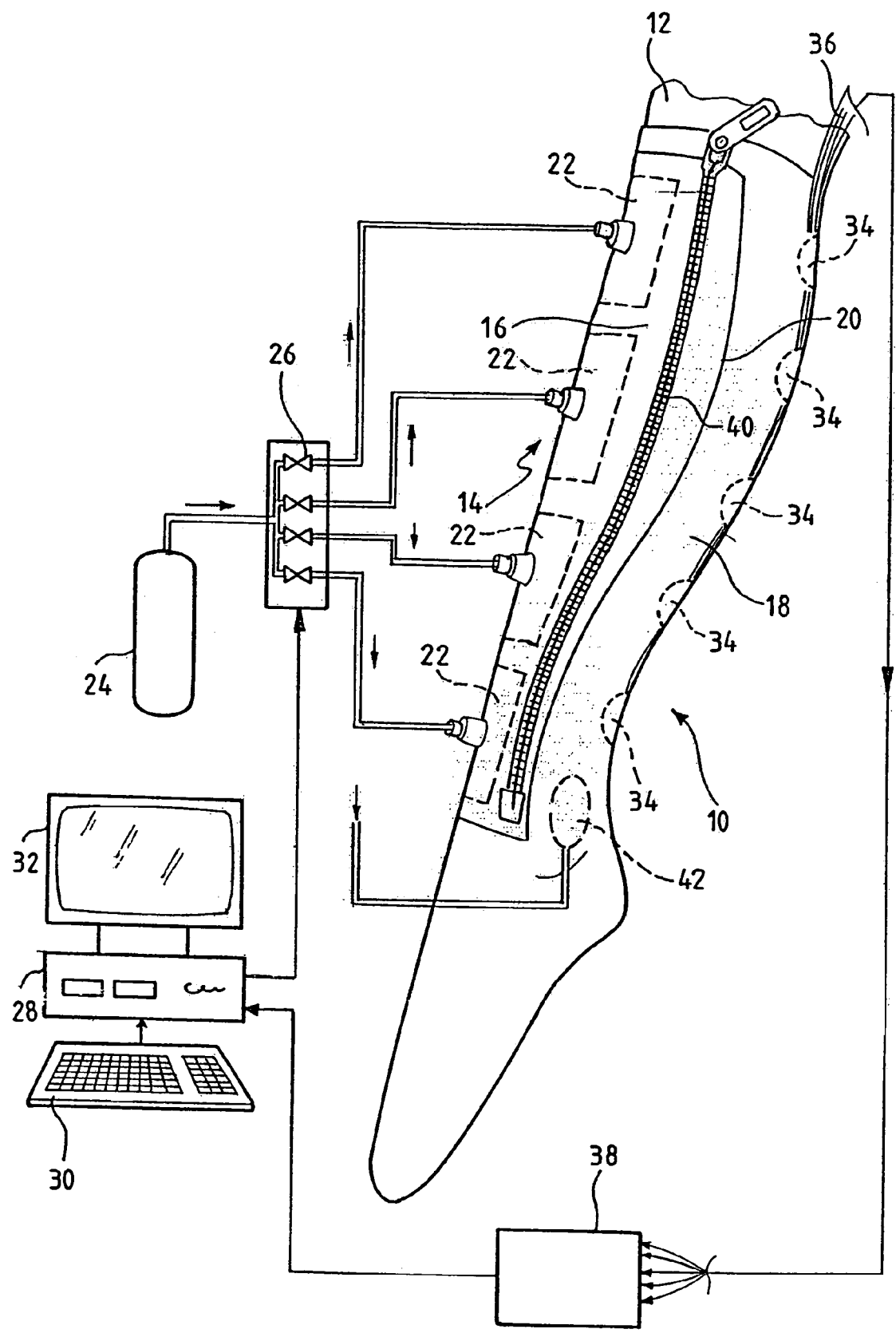

DEVICE FOR APPLYING CONTROLLED AND ADJUSTABLE COMPRESSION TO A LIMB

This is a national stage of PCT/FR03/01850 filed Jun. 18, 2003.

The present invention relates to a device for applying controlled and adjustable compression to a limb.

The invention is described mainly in the context of the compressing a lower limb, where that involves compressing the calf, i.e. the portion extending between the knee and the ankle, or compressing the entire leg from the ankle up to the top of the thigh.

Nevertheless, this application is not limiting, and the invention can equally well be applied to controlled and adjustable compression of an upper limb, for example for treating lymphedema of the arm or similar pathologies, whenever it is appropriate to envelop the limb in an adjustable compressive dressing.

The first object of the invention is to provide a study appliance capable of reproducing the effects of compression (where the term is used herein to mean physical compression produced by a compressive orthosis such as a sock, a stocking, or tights) on the venous flow in the leg of a subject, and to measure the effects thereof.

Such an instrument, intended for clinical experimentation performed by doctors, is intended to provide better knowledge about the hemodynamics of the lower limbs, in order to understand better the effects of therapeutic compression on venous circulation. The physiological mechanisms of venous pathologies can also be studied by acquiring clinical data (speed, flow rate, volume, pressure, etc.) from the lower limbs, with and without a compression system, and when a compression system is present, with different levels of compression and with different compression profiles along the height of the limb.

Nevertheless, this application to clinical experimentation is not limiting, and other applications are mentioned below where the device of the invention can be used in particularly advantageous manner.

More precisely, the invention provides such a device presenting various functional characteristics making it possible in particular:

- to apply adjustable compression over all or part of a subject's leg, typically compression that is degressive going upwards so as to encourage venous return to the upper portions of the organism, and above all so as to apply compression that is regular and progressive without any constriction or occlusion effect;
- to avoid forming an obstacle to investigating physical and physiological parameters such as measuring pressures or temperatures by means of sensors placed at various points on the leg, ultrasound measurements of the speeds of venous flows (Doppler examination), or of vein calibers (echographic examination), or indeed measurements of leg volume by plethysmography;
- to allow changes to the level and the profile of compression without interrupting the device, advantageously under computerized automatic control; and
- to replace in real time the measurements acquired on the subject, for subsequent computer processing.

Until now, clinicians have had few devices available that are genuinely effective in proceeding with that type of investigation.

Thus, proposals have been made to enclose the leg in an inflatable sleeve, or in a superposition of a plurality of inflatable sleeves at different pressures. Although that rudimentary technique enables approximate compression to be applied in certain cases for simple therapeutic purposes only, it is nevertheless not suited for undertaking a fine study of the physiological mechanisms of venous pathologies.

In particular, the pressure applied against the limb does not present a profile that is regular as is the case for a therapeutic orthosis where the pressure that is to be reproduced is degressive in regular manner going upwards. Furthermore, over a given perimeter, pressure is not applied uniformly since an inflated sleeve will form wrinkles leading to poor adherence on the leg and thus to irregular application of the compression force.

As described below, the invention enables all of those drawbacks to be mitigated and enables the intended objects to be achieved effectively, accurately, and with great flexibility of implementation.

To this end, the device of the invention comprises a tubular sleeve surrounding the limb, the sleeve comprising an anterior portion of inextensible or relatively inextensible material suitable for bearing against a relatively incompressible region of the limb, and a posterior portion of relative extensible material, suitable for covering the region of the limb that is to be compressed, the two portions being connected together substantially along two generator lines of the tubular sleeve forming connection generator lines. It also comprises a plurality of inflatable balloons disposed on the inside face of the anterior portion of the tubular sleeve along a generator line thereof situated at an intermediate position between the two connection generator lines between the two portions of the tubular sleeve, the balloons being suitable for being interposed between the inextensible material and said relatively incompressible region of the limb. Finally, means are provided for inflating each of the balloons in differing manner to respective given pressures, so as to apply deformation to the anterior portion of the sleeve that is suitable for inducing a traction force exerted on the extensible posterior portion, said force being distributed regularly along the connection generator lines and acting perpendicularly to said generator lines, said traction force thus giving rise to compression action on the compressible region of the limb.

According to various advantageous subsidiary characteristics:

- the anterior portion includes a zip fastener extending over a major fraction of the length of the sleeve;
- the anterior portion includes, at least over the top portion of the length of the sleeve, a closure enabling the diameter of the sleeve to be adjusted at a plurality of points;
- the material of the anterior portion and the material of the posterior portion are both knitted materials that are made together simultaneously by knitting;
- the device further comprises pressure sensors interposed between the material of the posterior portion and the limb to be compressed; in which case, the means for inflating each of the balloons in different manner may advantageously be means further controlled as a function of comparisons performed between the signals delivered by the pressure sensors and corresponding reference values that are a function of a desired pressure profile;
- the device further comprises at least one inflatable pouch disposed locally at a predetermined location of the posterior portion of the tubular sleeve, and suitable for filling in a concave portion of the region of the limb that is to be compressed; and
- the material of the posterior portion is a material that is transparent to ultrasound.

There follows a description in greater detail given with reference to the accompanying figure which shows an embodiment of the device of the invention together with the control and measurement means that are associated therewith.

In the FIGURE, reference 10 is an overall reference to the device of the invention which is used in the example shown for compressing the portion of the leg 12 that extends between the ankle and the top of the calf.

The device essentially comprises a tubular sleeve 14 that covers the calf, and that is in contact therewith over its entire area, like a sock. This tubular sleeve can be open or closed at its bottom end, i.e. it may optionally include a foot portion. In a variant embodiment, it may be extended upwards so that is also covers the knee and the thigh like a stocking, should it be desired to compress the lower limb over its full height.

The tubular sleeve 14 comprises two portions 16, 18 each extending over the full length of the working portion of the sleeve (i.e. the region to be compressed), and connected substantially along two generator lines 20 (only one of which can be seen in the figuer) situated on either side of the leg, one on the inside and the other on the outside).

The portion 16 is an anterior or front portion, and it extends along the ridge of the tibia, on which it is approximately centered axially. The other portion 18 is a posterior portion which essentially covers the compressible region of the limb, i.e. in the example shown, the region constituted by the calf muscle.

Preferably, the anterior portion 16 presents a peripheral extent that is smaller than that of the posterior portion 18, i.e. the two generator lines 20 where the two portions 16 and 18 join together are both located on the same anterior side of the limb.

The anterior portion 16 is made of a material that is essentially inextensible, or that has been made inextensible, but which is nevertheless sufficiently flexible to fit closely to the shape of the leg. By way of example, it is possible to use a rubber or a fabric that is slightly elastic, or indeed a knitted material of low elasticity. The inextensibility of this portion 16 may be increased, if necessary, by suitable stiffeners, such as the stiffeners inserted into gussets, or any other analogous known means.

In contrast, the posterior portion 18 is made of a material that is extensible, typically a knitted material presenting a stitch of the same type as is used in conventional elasticated stockings, for example Varisma (registered trademark) stockings from Innothera Topic. This stitch may be of the tuck, plain, micromesh, pinched, or float, etc., type, any stitch known to the knitting specialist, together with a cotton- and polyamide-covered elasthane yarn, an elasthane yarn covered in polyamide without cotton, or a mixture of elasthane and elastodiene, etc.

Incidentally, such a material presents the advantage of being transparent to ultrasound, thus enabling all of the usual investigations that are performed by echography or by Doppler techniques to be performed on the region of the limb that is covered by the posterior portion 18.

The "inextensible" or "relatively inextensible" nature of the anterior portion should naturally be understood in relative terms, as compared with the "extensible" nature of the posterior portion. More precisely, where the mode of action of the device of the invention is described below, the material of the anterior portion 16 needs to be selected in comparison with that of the posterior portion 18 so that the pressure exerted by the balloon 22 leads essentially to elastic deformation of the posterior portion 18 while the anterior portion 16 should serve solely for transmitting the traction force from the balloon 22 to the generator line 20 and consequently to the posterior portion 18. In other words, functionally speaking, the material of the anterior portion 16 serves essentially to transmit traction forces, while the material of the posterior portion 18 must essentially deform in elastic manner under the effect of traction, so as to apply pressure to the portion of the member that is covered by said posterior portion 18.

The two portions are assembled together along the two generator lines 20 by any appropriate method such as adhesive, hot textile bonding, or high frequency bonding. Advantageously, when the portions 16 and 18 are both of a knitted structure, instead of being made separately and then united, they are made simultaneously by being knitted together.

Interposed between the anterior portion 16 of the sleeve 14 and the tibial ridge of the limb, the device further comprises a succession of balloons 22, for example four rectangular balloons as shown, the long axes of the balloons being in alignment with one another and with the tibial ridge. The number and shapes of the balloons are nevertheless not limiting, and depend on the looked-for result (greater or lesser fineness in adjusting the pressure profile along the height of the limb), on the height that is to be compressed, etc., it being understood that functionally the balloons serve to put the material of the anterior portion 16 under tension, as described below.

These balloons 22 are connected to a source 24 of fluid under pressure, e.g. compressed air, via a series of valves 26 that are individually controlled so as to inflate each of the balloons to a given pressure. The valves 26 are solenoid valves under the control of a computer 28 running a program that defines a particular inflation profile. In conventional manner, the computer 28 is also provided with data input means such as a keyboard 30, and with display means such as a screen 32 for displaying control parameters and measurement results.

In the region of the limb that needs to be compressed, pressure sensors 34 are disposed at various levels between the leg and the posterior portion 18 of the sleeve 14 so as to measure the pressure that is produced locally. These sensors are themselves conventional (Saltzmann type sensors, or the like) and they are not described in greater detail. The signals they pick up are conveyed via wires united in a bundle 36 running along the inside of the tubular sleeve 14 and connected outside the device to an analog-to-digital converter 38 that is connected to an input of the computer 28.

In order to make the tubular sleeve 14 easy to put on, given the variety of leg shapes, and given sleeve flexibility that is less than that of an ordinary sock, because of the presence of the inextensible anterior portion 16 and the balloons 22, it is advantageous to provide a zip fastener 40 extending over the greater part of the length of the sleeve, so as to enable the sleeve 14 to be opened, e.g. in a region of the anterior portion 16 situated between the balloons and one of the generator lines 20.

The top portion of the sleeve may also be provided, likewise in its anterior portion with means (not shown) enabling the diameter of the sleeve to be adjusted at several levels, e.g. by hook & loop strip fasteners so as to be able to use the same device on subjects presenting morphologies, in particular in terms of ankle, calf, and/or thigh perimeter that can vary over large ranges (typically an ankle perimeter lying in the range 18 centimeters (cm) to 29 cm and a calf perimeter lying in the range 25 cm to 45 cm).

It is also possible to provide one or more inflatable pouches 42 placed between the leg and the material of the posterior portion 18 in regions such as the retromalleolar region or the sub-malleolar region. It can be desirable to fill in the corresponding concave portions so as to ensure that pressures are distributed more uniformly in the ankle region, for example when using a dressing with adjustable compression for treating venous ulcers. The function of the inflatable pouches 42 is nevertheless quite different from that of the balloons 22, and the inflatable pouch(es) 42 is/are of an entirely subsidiary nature.

There follows a description of the mechanism implemented by the invention.

By inflating the balloons 22 in controlled manner, they exert a traction effect that is distributed over the anterior portion 16 that is inextensible or extensible to a small extent only. The internal portion of each balloon rests against the tibial ridge, and this is a region of the limb that is practically incompressible. Since the balloon is interposed between two inextensible elements (the material of the anterior portion 16 and the tibial region of the limb), inflating the balloon will cause the material of the anterior portion 16 to move. This movement at the location of the tibial crest will be transmitted practically unchanged, given the inextensibility of the material to the generator line 20, where it will be converted into a traction force that is exerted on the deformable material of the posterior portion 18. The point at which this traction force is applied is located on the generator line 20, i.e. at the interface between the two portions 16 and 18, and the force acts in a direction that is substantially normal to the generator line, i.e. in a direction that is tangential to the perimeter of the leg at a given height therealong.

The magnitude of this force depends on the greater or lesser pressure to which the balloons 22 are inflated and can vary gradually along the entire height of the leg without any irregularity. In practice, it is found that the applied force presents a gradient that is very uniform even when using only a small number of balloons (e.g. only four balloons as in the example shown), and even if the pressure profile imposed by the inflation is an unconventional profile (e.g. progressive instead of being degressive). In particular, the profile that is obtained is not in any way "a staircase" type profile as has been the case with the rudimentary devices that have been proposed in the past.

This regularly distributed force is transmitted to the extensible material of the posterior portion 18 which transforms this force into a compression pressure that is exerted over the compressible posterior region of the limb, in a manner that is progressive and regular, in the same manner as could be obtained using an ordinary elasticated stocking.

The sensors 34 measure the pressure as applied in this way at various points.

Advantageously, inflation of the balloons 22 is servo-controlled to the signal coming from the sensors 34 so as to operate the solenoid valves 26 in such a manner as to obtain a pressure profile (as measured by the sensor 34) that is as close as possible to a predefined reference profile input into the software of the computer 28.

In practice, a device made in accordance with the teaching of the invention has made it possible to reproduce the effects of conventional physical compression means, i.e. stockings or tights in the range class I (10 millimeters of mercury (mmHg) to 15 mmHg, i.e. 13.3 hetopascals (hPa) to 20.0 hPa) to class III (20 mmHg to 36 mmHg, i.e. 26.6 hPa to 47.9 hPa). More generally, such a device is capable of reproducing relative pressures lying in the range 0 to 60 mmHg (0 to 80 hPa) with accuracy of ±1 mmHg (±1.33 hPa).

Numerous applications of the device of the invention can be envisaged other than experimental or statistical studies of the effects of compression applied to the lower limbs, in particular in the context of studying pathologies associated with chronic venous insufficiency (CVI). In particular, it can be of interest to register the pressures dynamically so as to evaluate variations in the effects of compression between resting and walking, etc. This application is made possible by the fact that the device of the invention does not require the leg to be immobilized in a fixed apparatus; on the contrary, the leg remains entirely free to move, and the only constraints are those associated with the pneumatic and electrical connections which can easily be designed so as to avoid impeding movements.

The invention makes it possible to envisage continuously recording pressures on outpatients over a long period. This applies in particular to long-haul flights when the leg swells during the flight and where it can be desirable to evaluate this swelling so as to apply compression that varies as a function of the way in which swelling varies.

Another application mentioned at the beginning of the description is that of dressings with adjustable compression, for example for treating venous ulcers of the leg where such compression greatly improves healing and resorption of the ulcer, or indeed for treating lymphedemia of the arm.

The device of the invention may also be used for teaching purposes, by causing the applied pressure profile to vary and displaying the results that is obtained, e.g. on an echographic or Doppler measurement.

The invention claimed is:

1. A device for applying controlled and adjustable compression to a limb, the device being characterized in that it comprises:
   a tubular sleeve (14) surrounding the limb (12), the sleeve comprising an anterior portion (16) of inextensible or relatively inextensible material suitable for bearing against a relatively incompressible region of the limb, and a posterior portion (18) of relative extensible material, suitable for covering the region of the limb that is to be compressed, the two portions being connected together substantially along two generator lines of the tubular sleeve forming connection generator lines (20);
   a plurality of inflatable balloons (22) disposed on the inside face of the anterior portion of the tubular sleeve along a generator line thereof situated at an intermediate position between the two connection generator lines between the two portions of the tubular sleeve, the balloons being suitable for being interposed between the inextensible material and said relatively incompressible region of the limb; and
   means (24, 26, 28) for inflating each of the balloons in differing manner to respective given pressures, so as to apply deformation to the anterior portion of the sleeve that is suitable for inducing a traction force exerted on the extensible posterior portion, said force being distributed regularly along the connection generator lines and acting perpendicularly to said generator lines, said traction force thus giving rise to compression action on the compressible region of the limb.

2. The device of claim 1, in which the anterior portion includes a zip fastener (40) extending over a major fraction of the length of the sleeve.

3. The device of claim 1, in which the anterior portion includes, at least over the top portion of the length of the sleeve, a closure enabling the diameter of the sleeve to be adjusted at a plurality of points.

4. The device of claim 1, in which the material of the anterior portion and the material of the posterior portion are both knitted materials that are made together simultaneously by knitting.

5. The device of claim 1, further including pressure sensors (34) interposed between the material of the posterior portion and the limb to be compressed.

6. The device of claim 5, in which the means for inflating each of the balloons in different manner are means further controlled as a function of comparisons performed between the signals delivered by the pressure sensors and corresponding reference values that are a function of a desired pressure profile.

7. The device of claim 1, further including at least one inflatable pouch (42) disposed locally at a predetermined location of the posterior portion of the tubular sleeve, and suitable for filling in a concave portion of the region of the limb that is to be compressed.

8. The device of claim 1, in which the material of the posterior portion is a material that is transparent to ultrasound.

* * * * *